US00PP31866P2

(12) United States Plant Patent
Farrow

(10) Patent No.: US PP31,866 P2
(45) Date of Patent: Jun. 16, 2020

(54) ***PIERIS* PLANT NAMED 'FARROWPJRF'**

(50) Latin Name: *Pieris japonica*
Varietal Denomination: FARROWPJRF

(71) Applicant: Michael W Farrow, Warwick, MD (US)

(72) Inventor: Michael W Farrow, Warwick, MD (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/501,065

(22) Filed: Feb. 14, 2019

(51) Int. Cl.
*A01H 5/02* (2018.01)
*A01H 6/36* (2018.01)

(52) U.S. Cl.
USPC ..... Plt./226

(58) Field of Classification Search
USPC ..... Plt./226
CPC ..... A01H 5/02; A01H 5/00; A01H 6/36
See application file for complete search history.

(56) References Cited

PUBLICATIONS

Spring Meadow Flowering Shrubs 2018-2019, retrieved on Oct. 8, 2019, retrieved at https://springmeadownursery.com/files/resource_files/2018-2019_SMN_Catalog_1-47.pdf cover page, pp. 1-9,17 and https://springmeadownursery.com/files/resource_files/2018-2019_SMN_Catalog_48-100.pdf, p. 72. (Year: 2019).*
University of Connecticut Plant Database Pieris japonica, retrieved on Oct. 9, 2019, retrieved from the Internet at http://www.hort.uconn.edu/plants/detail.php?pid=318, 4 pp. (Year: 2015).*

* cited by examiner

*Primary Examiner* — June Hwu
(74) *Attorney, Agent, or Firm* — Cassandra Bright

(57) ABSTRACT

A new and distinct *Pieris japonica* cultivar named 'FARROWPJRF' is disclosed, characterized by intense, long-lasting pink flower color. Plants are compact and dense. The new cultivar is a *Pieris*, suitable for ornamental garden purposes.

4 Drawing Sheets

Latin name of the genus and species: *Pieris japonica.*
Variety denomination: 'FARROWPJRF'.

BACKGROUND OF THE INVENTION

The new cultivar is a product of a planned breeding program by the inventor, Michael Farrow. The objective of this program was to produce improved flower colors, and compact, refined plant growth habits. The open pollination was conducted in 2004 at a nursery in Earleville, Md. This new variety, hereinafter referred to as 'FARROWPJRF', was discovered and selected at the same nursery in Earleville, Md. during 2008. The female parent is *Pieris japonica* 'Dorothy Wyckoff', unpatented. The male parent is unidentified.

After identifying the new variety as a potentially interesting selection, softwood cuttings were taken at the nursery in Earleville, Md., then taken to a commercial nursery in Grand Haven, Mich. for rooting in 2008. The inventor continued controlled testing and propagation, assessing stability of the unique characteristics of this variety. Ten generations have been reproduced and have shown that the unique features of this cultivar are stable and reproduced true to type. First public access to plants of the variety occurred during August of 2018 in the United States. This offer came directly or indirectly from the inventor, qualifying for the exception allowed under 102(b). Previous to this sale, although the variety may have been publicized in print, plants were not available to the public for propagation.

SUMMARY OF THE INVENTION

The cultivar 'FARROWPJRF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'FARROWPJRF' These characteristics in combination distinguish 'FARROWPJRF' as a new and distinct *Pieris japonica* cultivar:

1. Intense pink flower color.
2. Long lasting flower color.
3. Compact and dense plants.

PARENT COMPARISON

Plants of the new variety of *Pieris japonica* 'FARROWPJRF' are similar to plants of the seed parent variety of *Pieris japonica* 'Dorothy Wyckoff', unpatented, in most horticultural characteristics; however, plants of 'FARROWPJRF' differ in the following:

1. New cultivar has intense pink flowers; seed parent has pale pink to white flowers.

COMMERCIAL COMPARISON

'FARROWPJRF' can be compared to the commercial variety *Pieris japonica* 'Valley Valentine', unpatented. The varieties are similar in most horticultural characteristics, however, plants of 'FARROWPJRF' differ in the following ways:

1. New variety's flowers are an intense pink color; comparator has light red flowers.
2. New cultivar is a denser plant than this comparator.

BRIEF DESCRIPTION OF THE PHOTOGRAPHS

The accompanying photograph in FIG. 1 illustrates in full color a typical plant of 'FARROWPJRF' in a 3 gallon container grown during Summer in Grand Haven, Mich. in a polyhouse. Plants in FIG. 1 are approximately 2 to 3 years old.

Figure 1:
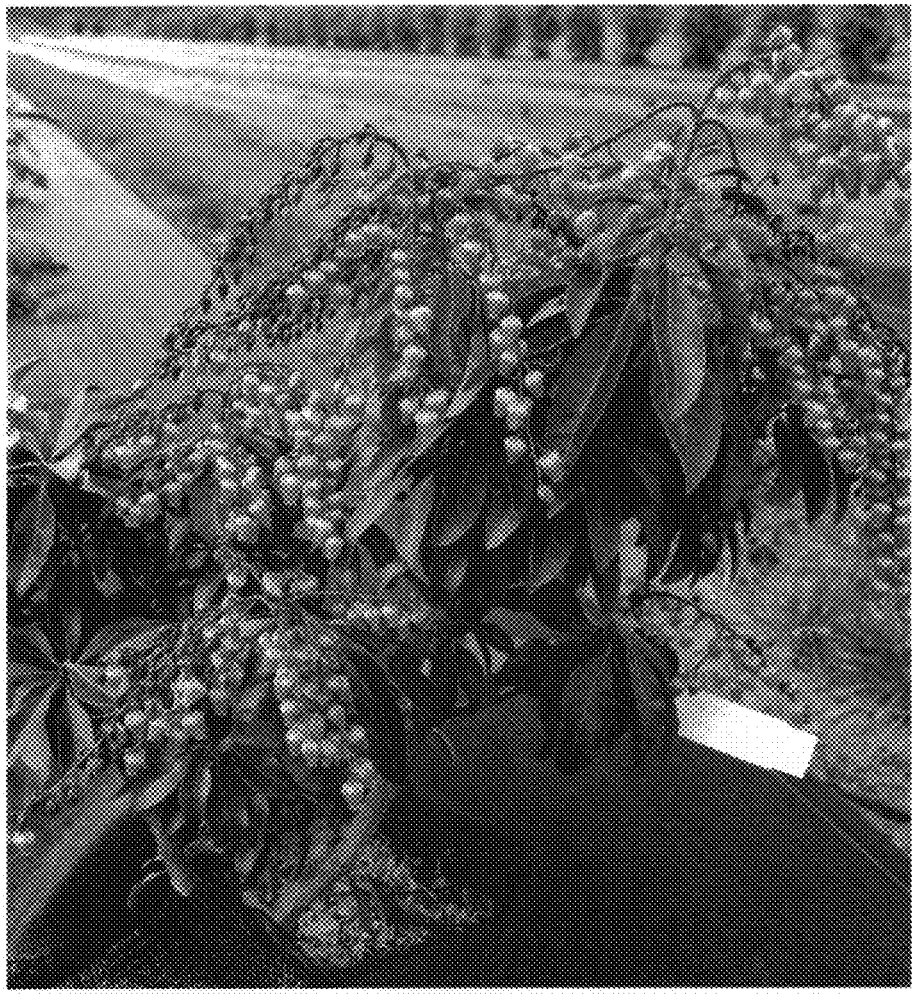
Figure 2:
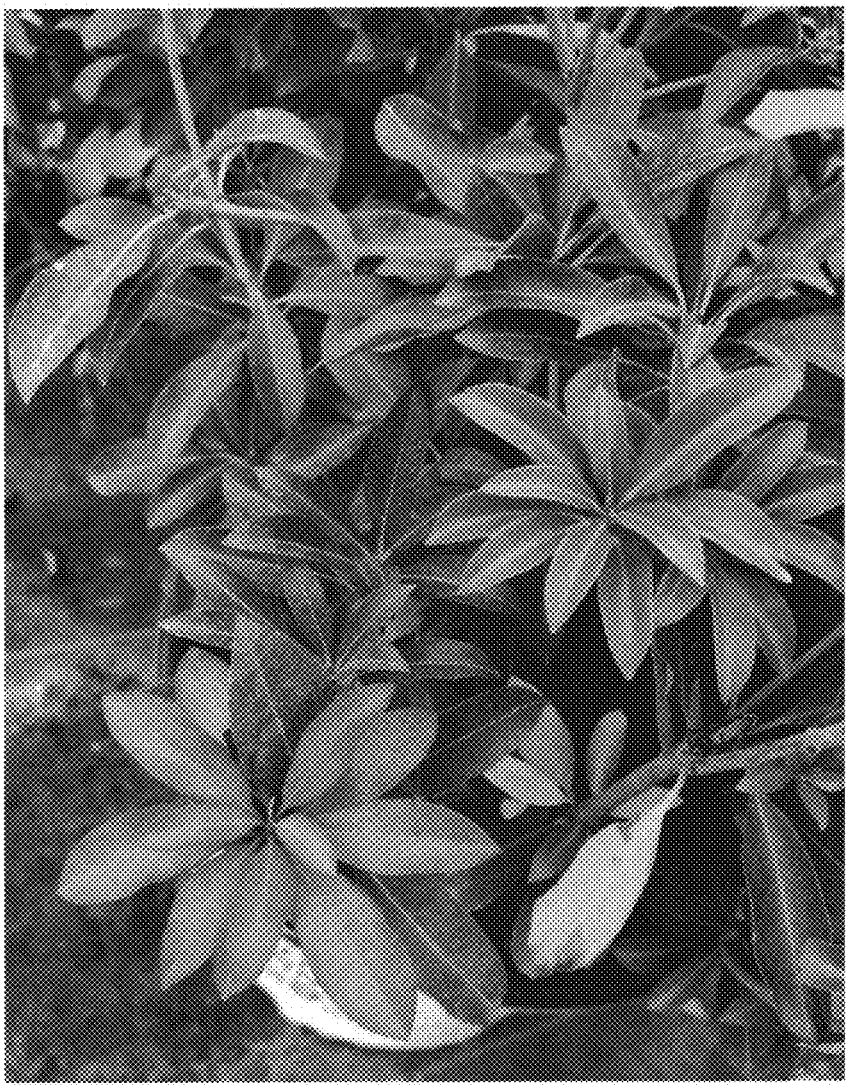
FIG. 2 illustrates a close up view of the foliage, including the red new growth during early Spring in Grand Haven, Mich.
Figure 3:
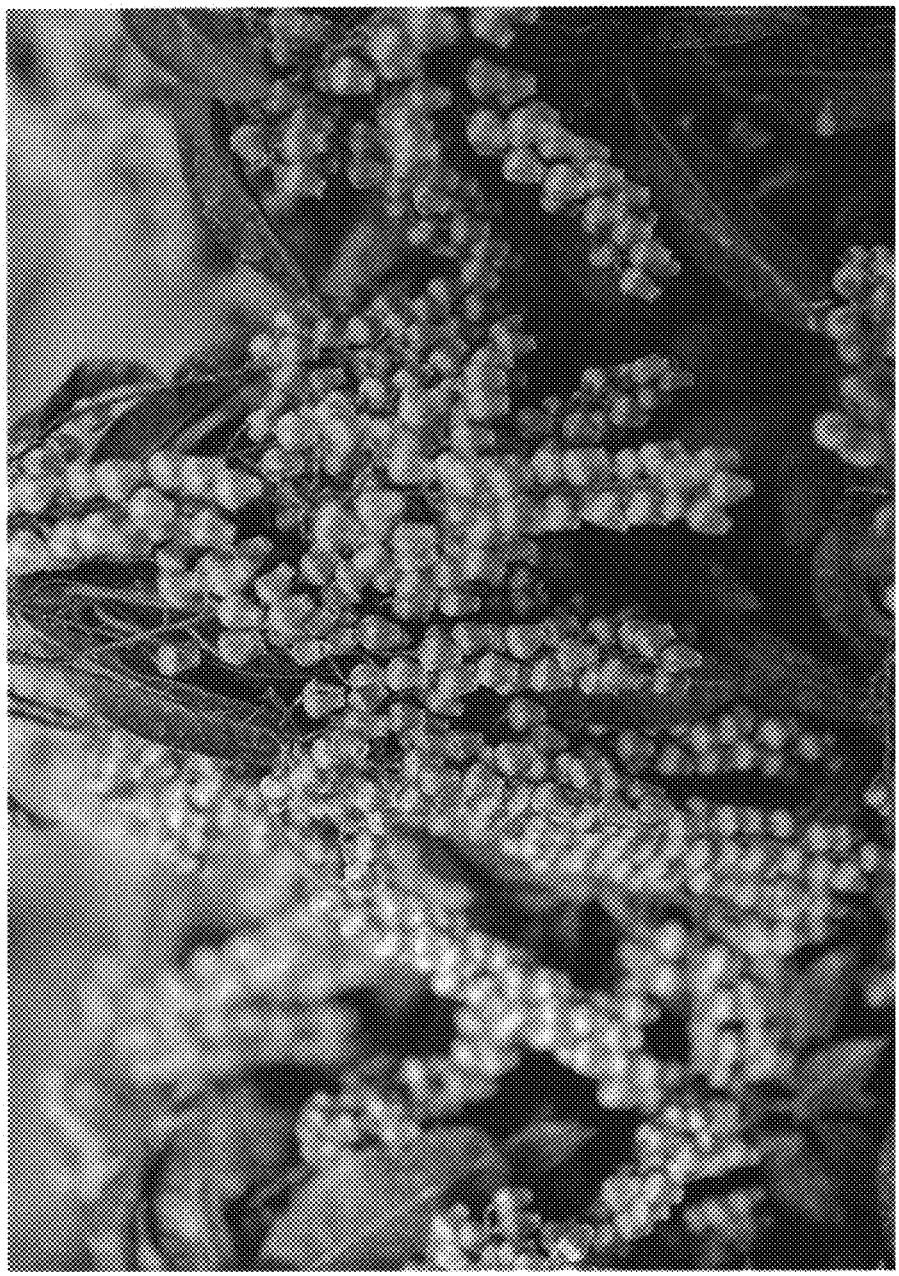
FIG. 3 illustrates a close up view of the inflorescence during Summer in Grand Haven, Mich.
Figure 4:
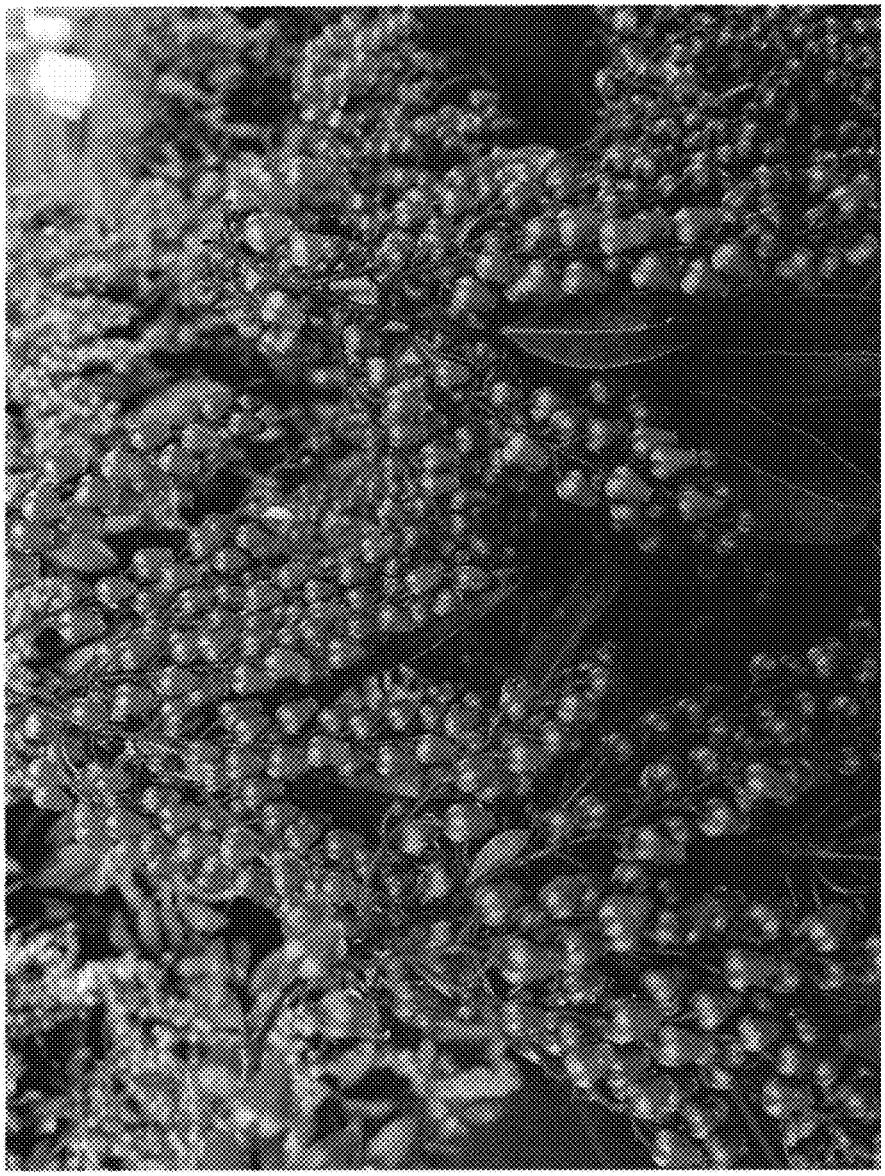
FIG. 4 illustrates a close up view of the newly opened inflorescence, taken March 16 in Grand Haven, Mich.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'FARROWPJRF' plants grown in a poly greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types. Botanical classification: *Pieris japonica* 'FARROWPJRF'.

PROPAGATION

Typical method: Softwood cuttings.
Time to initiate rooting: 7 to 9 weeks at approximately 10° C.
Root description: Fibrous, thin, moderately dense, moderately well branched. Colored white to light brown, not accurately measured with an R.H.S. chart.

PLANT

Age of plant described: 2-3 years.
Container size of plant described: 3-gallon pot.
Growth habit: Upright evergreen flowering shrub.
Height: 50 cm.
Plant spread: 60 cm.
Pinching required: Some.
Branching characteristics:
Angle: 45 to 80° from center.
Quantity of lateral branches: Typical range 25 to 40.
Length of lateral branches: 35 cm.
Diameter of lateral branches: 5 mm.
Lateral branch shape: Round.
Stem strength: Strong.
Stem color: RHS Yellow-Green 145A, flushed near Red 46D.
Internode length: Average 5 mm.
Bark description: Oldest wood peels in long, thin strips. Younger bark scaly. Oldest bark colored near Grey-Brown 199A. Younger bark near Greyed-Green 197B.

FOLIAGE

Leaf:
- *Arrangement.*—Sub-alternate, single. Terminal foliage whorled.
- *Shape of blade.*—Narrowly elliptic.
- *Average length.*—4 cm.
- *Average width.*—1.5 cm.
- *Apex.*—Acute.
- *Base.*—Cuneate.
- *Margin.*—Serrate.
- *Texture of top surface.*—Smooth, slightly waxy.
- *Texture of bottom surface.*—Smooth.
- *Appearance of top surface.*—Young foliage moderately glossy, mature foliage matte.
- *Appearance of bottom surface.*—Matte.
- *Foliage color.*—Young foliage upper side: Emerging RHS Orange-Red N34A, flushed Yellow 12A, turning Greyish Green NN137B. Young foliage under side: Emerging RHS Orange-Red 34A, flushed Yellow 12A, turning Yellow-Green 146B. Mature foliage upper side: RHS Greyish Green NN137B. Mature foliage under side: RHS Yellow-Green 146B.
- *Venation.*—Pinnate.
- *Venation color.*—Upper Side: RHS Yellow-Green 144C. Under Side: RHS Yellow-Green 144C.
- *Fragrance.*—Not observed.

Petiole:
- *Texture, upper side.*—Smooth.
- *Texture, under side.*—Smooth.
- *Color, upper side.*—RHS Yellow-Green 144C base flushed 53C. New growth petioles colored near Red 43B on upper surface, lower surface petioles near Red 41B.
- *Color, under side.*—RHS Yellow-Green 144C base flushed 53C.

Stipules:
- *Length.*—2 mm.
- *Color.*—RHS Greyed-Red 181C.

FLOWER

Bloom period: Begins flowering in early Spring, early to mid-March in Grand Haven, Mich. Flowering continues through Summer.
Inflorescence:
- *Type/form.*—Raceme.
- *Height.*—7 cm.
- *Width.*—2 cm.
- *Flowers per inflorescence.*—10-28.
- *Habit.*—Multiple inflorescences stemming from single stem. Individual flowers pendulous, inflorescence long and arching.
- *Flowers per lateral stem.*—10 inflorescences per stem. Average range 20 to 50 flowers per inflorescence.

Fragrance: None.
Bud:
- *Shape.*—Oval.
- *Length.*—5 mm.
- *Diameter.*—2 mm.

*Color*.—Summer: RHS Yellow-Green N144A with some Greyed-Purple 183C. Fall/Winter: RHS Red-Purple 59A.

Flower:

*Aspect*.—Pendulous.

*Shape*.—Urceolate, with reduced petal lobes.

*Length*.—7 mm.

*Diameter*.—6 mm.

*Persistent or self-cleaning*.—Self-cleaning.

Corolla tube and petal lobes:

*Petal lobe arrangement*.—Radially around bell-shaped corolla tube.

*Tube length*.—7.5 mm.

*Tube diameter*.—4-5 mm.

*Petal lobe quantity*.—5.

*Petal lobe length*.—About 1-2 mm.

*Petal lobe diameter*.—About 1.5 mm.

*Petal lobe shape*.—Ovate.

*Corolla tube overall shape*.—Broad conical.

*Texture*.—Outer Surface: Smooth, glabrous. Inner Surface: Smooth, glabrous.

*Petal lobe apex*.—Obtuse.

*Base*.—Fused.

*Corolla tube color*.—Opening: Outer surface: RHS Red-Purple 58B. Base Red 38B. Inner surface: Upper 40% RHS Red-Purple 58B, lower 50% Purple 75B. Fully opened: Outer surface: RHS Red-Purple 67B. Base White 155A. Inner surface: Upper 40% RHS Red-Purple 67B, lower 50% Red 55C. Fading (only with age): Outer and inner surface: Near RHS White N155B.

*Petal lobe color*.—Opening: Outer surface: RHS Red 38D. Inner surface: RHS Red 38D. Fully opened: Outer surface: RHS Red 56D. Inner surface: RHS Red 56D. Fading (only with age): Outer and inner surface: Near RHS White N155B.

Sepal:

*Arrangement*.—Single whorl.

*Number*.—5.

*Shape*.—Ovate.

*Tip*.—Acute.

*Base*.—Cuneate.

*Margin*.—Entire.

*Length*.—3 mm.

*Width*.—1.5 mm.

*Texture, upper side*.—Smooth, glabrous.

*Texture, under side*.—Smooth, glabrous.

*When opening*.—Color, Upper Side: RHS Red-Purple 60C, fading to White 155A along margins. Color, Under Side: RHS Red-Purple 60C, fading to White 155A along margins.

*Fully open*.—Color, Upper Side: RHS Yellow-Green 154D, fading to White 155A along margins. Color, Under Side: RHS Yellow-Green 154D, fading to White 155A along margins.

Peduncle:

*Length*.—10 cm.

*Diameter*.—2 mm.

*Angle*.—Approximately 80°.

*Strength*.—Strong.

*Texture*.—Smooth, glabrous.

*Color*.—RHS Red-Purple 60B.

Pedicel:

*Length*.—4 mm.

*Diameter*.—1.5 mm.

*Angle*.—40-80°.

*Strength*.—Strong.

*Texture*.—Smooth, glabrous.

*Color*.—RHS Red-Purple 60B.

REPRODUCTIVE ORGANS

Stamens:

*Number*.—10.

*Filament length*.—4 mm.

*Filament color*.—RHS Black 200A.

*Anthers*.—Shape: Oval. Length: 1 mm. Pollen: Scarce. Pollen Color: RHS Greyed-Orange 167C.

*Pistil*.—Number: 1. Length: 5 mm.

*Stigma*.—Shape: Round. Color: RHS White 155D. Style Length: 4 mm. Style Color: RHS White 155D. Ovary Color: RHS White 155D.

OTHER CHARACTERISTICS

Disease and pest resistance: Neither resistance nor susceptibility observed.

Drought tolerance: No tolerance for drought.

Temperature tolerance: −29 to 36° C.

What is claimed is:

1. A new and distinct cultivar of *Pieris japonica* plant named 'FARROWPJRF' as herein illustrated and described.

* * * * *